United States Patent [19]

Mascarenhas et al.

[11] Patent Number: 5,470,727
[45] Date of Patent: Nov. 28, 1995

[54] CHROMOSOMAL EXPRESSION OF NON-BACTERIAL GENES IN BACTERIAL CELLS

[75] Inventors: Desmond Mascarenhas, San Rafael; Pamela S. Olson, Cupertino, both of Calif.

[73] Assignee: Celtrix Pharmaceuticals, Inc., Santa Clara, Calif.

[21] Appl. No.: 170,588

[22] Filed: Dec. 21, 1993

[51] Int. Cl.$^6$ ............................ C12N 15/64; C12N 15/66
[52] U.S. Cl. .................................. 435/172.3; 435/91.4
[58] Field of Search ........................ 435/172.3, 252.3, 435/320.1, 252.33, 91.4; 536/23.1

[56] References Cited

U.S. PATENT DOCUMENTS

| | | | |
|---|---|---|---|
| 4,425,437 | 1/1984 | Riggs | 435/320.1 |
| 4,431,739 | 2/1984 | Riggs | 435/252.3 |
| 4,563,424 | 1/1986 | Riggs | 435/69.4 |
| 4,704,362 | 11/1987 | Itakura et al. | 435/252.3 |
| 5,196,318 | 3/1993 | Baldwin et al. | 435/69.1 |

OTHER PUBLICATIONS

Diederich et al. (1992), Plasmid 28: 14–24.
Goeddel, ed., *Methods in Enzymology*, Academic Press, Inc., San Diego, vol. 185. Pp. i–ix.
Dulbecco et al., eds., *Virology* (1988) Lippincott Publishers, Philadelphia pp. 56–57.
Borck et al., "The construction in vitro of transducing derivatives of phage lambda" *Molec. gen. Genet.* (1976) 146:199–207.
Struhl et al., "Functional genetic expression of eukaryotic DNA in *Escherichia coli*" *Proc. Natl. Acad. Sci. USA* (1976) 73:1471–1475.
Greener et al., "Identification of a novel genetic element in *Escherichia coli* K–12" *J. Bacteriol.* (1980) 144:312–321.
Russel et al., "Construction and characterization of glutaredoxin–negative mutants of *Escherichia coli*" *Proc. Natl. Acad. Sci. USA* (1988) 85:990–994.
Struhl et al., "Production of a functional eukaryotic enzyme in *Escherichia coli*: Cloning and expression of the yeast structural gene for imidazole–glycerolphosphate dehydratase (*his3*)" *Proc. Natl. Acad. Sci. USA* (1977) 74(12):5255–5259.

Primary Examiner—Mindy B. Fleisher
Assistant Examiner—Philip W. Carter
Attorney, Agent, or Firm—Morrison & Foerster

[57] ABSTRACT

The present invention provides compositions and methods for inserting a copy of a heterologous gene into the chromosome of a host cell such as *E. coli* through the use of a chromosomal transfer DNA, a circular, non-self-replicating DNA carrying a site-specific recombination site such as lambda att P. The host cell chromosome contains a second site-specific recombination site. When the chromosomal transfer DNA is introduced into the host cell, expression of an integration enzyme such as integrase causes the integration of the chromosomal transfer DNA into the host cell chromosome at the second recombination site.

1 Claim, 9 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CCCATCGATG CATTAAGCGG ATTTAGCCGG TTTCAG    36

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCCTGACTGC GTTAGCAATT TAACTGTGAT    30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTGGGCTGCT TCCTAATGCA GGAGTCGCAT    30

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TAATACGACT CACTATAGGG AGA    23

( 2 ) INFORMATION FOR SEQ ID NO:5:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GATCTGTTGA CAATTAATCA TCGAACTAGT TAACTAGTAC GCAAGTT    47

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGCTAGTTAT TGCTCAGCGG    20

( 2 ) INFORMATION FOR SEQ ID NO:7:

-continued ( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CAGGATCCGA TCGTGGAGGA TGATTAAATG GCGAAAGGGG ACCCGCAC     48

( 2 ) INFORMATION FOR SEQ ID NO:8:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CAGGAAGCTT ACGGCAGGAC TTTAGCGGAA AG     32

( 2 ) INFORMATION FOR SEQ ID NO:9:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

GGGGCCGCGG TGGCATGCAG ATTTTCGTCA AGACTTTGA     39

CHROMOSOMAL EXPRESSION OF NON-BACTERIAL GENES IN BACTERIAL CELLS

TECHNICAL FIELD

This invention is related to the field of expression of heterologous genes in bacteria.

BACKGROUND ART

A gene carried on one of the multicopy plasmids commonly used for cloning and expressing foreign proteins in *E. coli* usually has a copy number of more than 20 copies/cell. Even low copy number plasmids (e.g., pACYC177 and pLG339) generally exist at 6–10 copies per cell. The expression of even minute amounts of some foreign proteins can kill host cells (see *Meth. Enzymol.* 185:63–65, ed. D. Goeddel, 1990). For this reason, it would be advantageous to reliably limit the copy number of genes encoding such toxic gene products, such as by integrating the gene into the bacterial chromosome at one or a small number of copies per cell. For example, such a system would allow one to make more representative cDNA expression libraries in bacterial hosts if the high-copy expression of one or more of the cDNAs in the library could kill the bacterial host or cause it to grow poorly.

Chromosomal integration of genes encoding heterologous polypeptides would also be advantageous as an alternative means for expression of foreign proteins in bacterial host cells. Multicopy vectors are often unstable and require the use of antibiotics in the growth medium for maintenance. Present methods of integrating foreign genes into the bacterial chromosome suffer from inefficiency, the inability to control the site of integration of the foreign gene, and/or the inability to control the copy number of the integrated gene. Most importantly, all efforts to date to create recombinant DNA constructs on the bacterial chromosome, wherein a bacterial promoter is fused to a heterologous gene, have involved the creation of viral or plasmid intermediates carrying the construct. Because such intermediates replicate at high copy number, they may be difficult or even impossible to recover in cases where the foreign gene product is toxic to the bacterial cell.

Previous methods for achieving the integration of foreign genes into the chromosome of a bacterial host include the use of phage λ vectors. The phage DNA in circular form is inserted linearly into the bacterial chromosome by a single site specific recombination between a phage attachment site (att P), 240 bases long, and a bacterial attachment site (att B), only 25 bases long. The two sites have 15 bases in common. This site-specific recombination event is catalyzed by a special integrase, specified by the phage gene INT (Virology, 2nd ed., R. Dulbecco and H. Ginsberg, eds., Philadelphia: Lippincott, pp. 56–57 (1985)).

Phage vectors which are INT⁻ can be integrated into the chromosome in a normal fashion as long as integrase is supplied in trans, e.g., by an INT⁺ helper phage (see, e.g., Borck et al. (1976) *Molec. Gen. Genet.* 146:199–207).

Phage vectors which are both att⁻ and INT⁻ can likewise be integrated into the bacterial chromosome as double lysogens by using att⁺INT⁺ helper phage. Double lysogens formed by linkage of the prophages at the bacterial attachment site are integrated into the chromosome by general bacterial recombination between homologous sequences on the defective phage and on the helper phage (see, e.g., Struhl et al. (1976) *Proc. Natl. Acad. Sci. USA* 73:1471–1475).

Similarly, it is also possible to integrate non-replicating colE1 replicons into the genome of polA strains of *E. coli* by means of recombination between the host chromosome and homologous sequences carried by the plasmid vector (Greener and Hill (1980) *J. Bacteriol.* 144:312–321).

DISCLOSURE OF THE INVENTION

The present invention provides compositions and methods for inserting a copy of a heterologous gene into the chromosome of a host cell such as *E. coli* through the use of a chromosomal transfer DNA, a circular, non-self-replicating DNA carrying a site-specific recombination site. The host cell chromosome contains a second site-specific recombination site. When the chromosomal transfer DNA is introduced into the host cell, expression of an integration enzyme such as integrase causes the integration of the chromosomal transfer DNA into the host cell chromosome at the second recombination site.

The present invention therefore provides a chromosomal transfer system comprising:

a chromosomal transfer DNA comprising a gene of interest operably linked to a promoter functional in a host cell, a selectable marker, and a first recombination site, and lacking an origin of replication; and the host cell, preferably a bacterial cell such as *E. coli*, comprising a chromosome, the chromosome comprising a second recombination site, and a DNA sequence encoding an enzyme which is capable of catalyzing the site-specific recombination of the first and second recombination sites;

whereby introduction of the chromosomal transfer DNA into the host cell and expression of the enzyme results in integration of the chromosomal transfer DNA into the chromosome of the host cell at the second recombination site;

and whereby the gene of interest is at no time operably linked to a functional promoter in a multicopy number vector.

The first recombination site of the chromosomal transfer DNA is preferably att P or att B, the second recombination site is preferably att P or att B, and the enzyme is preferably integrase.

The present invention also provides a set of vectors useful in constructing a chromosomal transfer DNA comprising a first and a second plasmid vector capable of replication in a host cell, the first plasmid vector comprising a first origin of replication, and a foreign gene of interest lacking an operably linked promoter;

the second plasmid vector comprising a second origin of replication, and a promoter;

wherein the origins of replication and the promoter are functional in the host cell, and wherein either said first plasmid or said second plasmid comprises a recombination site; and whereby ligation of a restriction fragment from each of the first and second vectors produces a chromosomal transfer DNA.

Also provided are methods for introducing a gene of interest into a chromosome of a host cell which employ such a chromosomal transfer DNA. Such methods comprise the steps of:

transferring a chromosomal transfer DNA comprising a gene of interest, a selectable marker, and a first recombination site and lacking an origin of replication into a host cell, the host cell comprising a chromosome, the chromosome comprising a second recombination site, and a DNA sequence encoding an enzyme which is capable of catalyzing the site-specific recombination of the first and second recombination sites;

expressing the enzyme, thereby causing integration of the chromosomal transfer DNA into the chromosome of the host cell at the second recombination site; and selecting for host cells having an integrated chromosomal transfer DNA;

whereby the gene of interest is at no time operably linked to a functional promoter in a multicopy number vector.

Such methods may further comprise the step of ligating a restriction fragment from each of the first and second plasmid vectors, thereby producing the chromosomal transfer DNA.

MODES FOR CARRYING OUT THE INVENTION

Figure 1:
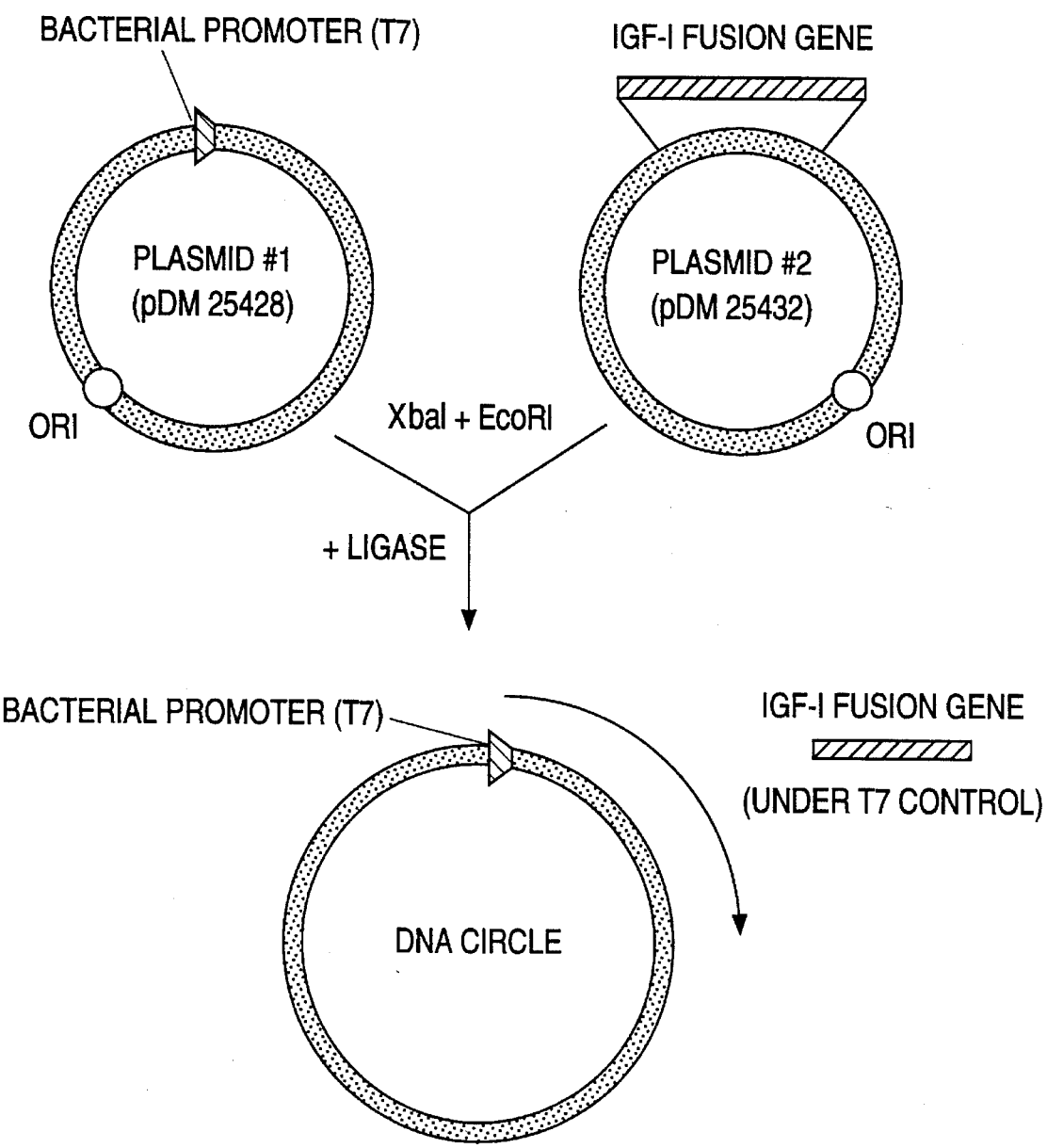
FIG. 1 shows steps in the in vitro formation of a chromosomal transfer DNA, a DNA circle which lacks an origin of replication (and thus is incapable of self-replication) and is suitable for integration of a foreign gene into the bacterial chromosome. Until the chromosomal transfer DNA is formed, the foreign gene to be expressed (here an IGF-1 fusion gene) is separated from a functional bacterial promoter (here the T7 promoter).

The present invention employs "chromosomal transfer DNA," which may be used to simply, efficiently, and reliably insert a copy of a heterologous gene into the chromosome of a host cell, e.g., E. coli. A chromosomal transfer DNA is a circular DNA comprising a gene of interest, a selectable marker (e.g., an antibiotic resistance gene), and a recombination site (e.g., lambda att P or att B), and lacking an origin of replication or autonomously replicating sequence (ARS). The chromosomal transfer DNA is therefore incapable of replicating independently when introduced into the host cell.

When a chromosomal transfer DNA is introduced into a host cell having a chromosome which contains a second, similar recombination site (e.g., another att P or att B site), expression in the host cell of an enzyme which is capable of catalyzing the site-specific recombination of the recombination sites (e.g., integrase) results in the integration of the vector into the host cell chromosome at the recombination site. This site-specific recombination process is much more efficient than general recombination systems acting on homologous vector and host chromosomal sequences and results in integrated sequences having greater stability, particularly when integrase synthesis can be controlled. Integrase may also be provided by a plasmid or other DNA molecule transiently or stably present in the host cell at the time when the chromosomal transfer DNA is introduced.

An important feature of this approach is that the gene of interest is at no time operably linked to a functional promoter on a multicopy vector. By keeping a functional promoter separated from the gene of interest until the foreign gene is safely present in the cell at low copy number, the potential toxic or lethal effects of the gene product can be minimized.

Alternatively, high level expression of less toxic gene products can be accomplished by multiple integrations or by amplification of integrated genes.

Introduction of a chromosome transfer DNA into the chromosome of E. coli at from 1–3 copies per cell and expression of a foreign gene (IGF-I fusion protein) carried on the chromosomal transfer DNA is described in the Example below.

Recombinant DNA Methods and Reagents

General techniques for nucleic acid manipulation useful for the practice of the claimed invention are described generally, for example, in *Molecular Cloning: A Laboratory Manual,* 2d ed., Vols. 1–3, ed. Sambrook, et al., Cold Spring Harbor Laboratory Press (1989); or *Current Protocols in Molecular Biology,* ed. F. Ausubel et al., Greene Publishing and Wiley-Interscience: New York, 1987 and periodic updates. Reagents useful in nucleic acid manipulation, such as restriction enzymes, T7 RNA polymerase, DNA ligases and so on are commercially available from such vendors as New England BioLabs, Boehringer Mannheim, Amersham, Promega Biotec, U.S. Biochemicals, and New England Nuclear.

Definitions

"Foreign" or "heterologous"; "native" or "homologous

A "foreign" or "heterologous" polypeptide is a polypeptide which is not normally found in a host cell of a particular species. The nucleic acid encoding such a polypeptide is also referred to as "foreign" or "heterologous." For example, insulin-like growth factor (IGF), a mammalian polypeptide, is native to mammalian cells but foreign or heterologous to E. coli. A "native" or "homologous" polypeptide or DNA sequence, by contrast, is commonly found in the host cell. A promoter or other sequence affecting, for example, the transcription or translation of a gene is also considered "homologous" if it is functional in the host cell. For example, a T7 promoter is considered "homologous" to an *E. coli* host cell, since, if T7 RNA polymerase is present in the cell, the T7 promoter is capable of driving the transcription of a polypeptide-encoding sequence to which it is operably linked.

"Encode"

A nucleic acid is said to "encode" a polypeptide if, in its native state or when manipulated by recombinant DNA methods, it can be transcribed and/or translated to produce the polypeptide.

"Operably linked"

A nucleic acid sequence is operably linked when it is placed into a functional relationship with another nucleic acid sequence. For example, a promoter is operably linked to a coding sequence if the promoter affects its transcription or expression. Generally, DNA sequences which are operably linked are contiguous and, where necessary, in reading frame.

"Recombinant"

A "recombinant" nucleic acid is one which is made by the joining of two otherwise separated segments of nucleic acid sequence in vitro or by chemical synthesis.

Probes and Primers

Nucleic acid probes and primers are isolated nucleic acids, generally single stranded, and, especially in the case of probes, are typically attached to a label or reporter molecule. Probes are used, for example, to identify the presence of a hybridizing nucleic acid sequence in a tissue or other sample or in a cDNA or genomic clone in a library. Primers are used, for example, for amplification of nucleic acid sequences, e.g., by the polymerase chain reaction (PCR). The preparation and use of probes and primers is described, e.g., in Sambrook et al. (1989) or Ausubel et al. (1987).

Chemical Synthesis of Nucleic Acids

Nucleic acids, especially short nucleic acids such as amplification primers, may be produced by chemical synthesis, e.g., by the phosphoramidite method described by Beaucage and Carruthers (1981) *Tetra Letts.* 22:1859–1862 or the triester method according to Matteucci et al. (1981) *J. Amer. Chem. Soc.* 103:3185, and may be performed on automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Features of Chromosomal Transfer DNA and of Plasmids Used in Their Construction

Chromosomal transfer DNA comprises a DNA fragment encoding a selectable marker and a sequence encoding a desired foreign polypeptide operably linked to transcription and translational initiation regulatory sequences and expression control sequences, which may include a promoter, an enhancer and necessary processing information sites, such as ribosome-binding sites, and mRNA stabilizing sequences, as well as any necessary secretion signals, where appropriate, which allow the protein to cross and/or lodge in cell membranes, and thus attain its functional topology, or be secreted from the cell.

Plasmids used in construction of a chromosomal transfer DNA will also typically comprise a replication system recognized by the host, including an origin of replication or autonomously replicating sequence (ARS).

Chromosomal transfer DNA may be prepared from such vectors by means of standard recombinant techniques well known in the art and discussed, for example, in Sambrook et al. (1989) or Ausubel et al. (1987).

An appropriate promoter and other sequences necessary for efficient transcription and/or translation are selected so as to be functional in the host cell. Examples of workable combinations of cell lines and expression vectors are described in Sambrook et al. (1989) or Ausubel et al. (1987); see also, e.g., Metzger et al. (1988) *Nature* 334:31–36. Promoters such as the trp, lac and phage promoters (e.g., T7, T3, SP6), tRNA promoters and glycolytic enzyme promoters are useful in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. See, e.g., Hitzeman et al. EP 73,657A. Appropriate mammalian promoters include the early and late promoters from SV40 (Fiers et al. (1978) *Nature* 273:113) or promoters derived from murine Molony leukemia virus, mouse mammary tumor virus, avian sarcoma viruses, adenovirus II, bovine papilloma virus or polyoma virus. In addition, the construct may be joined to an amplifiable gene (e.g., DHFR) so that multiple copies of the gene may be made, where desired. For appropriate eukaryotic enhancer and other expression control sequences, see, e.g., *Enhancers and Eukaryotic Gene Expression*, Cold Spring Harbor Press: New York, 1983.

It is preferable that the promoter driving expression of the foreign gene when integrated in the chromosome of the host is controllable.

Chromosomal transfer DNAs and plasmids employed in their construction comprise a selectable marker, a gene encoding a protein necessary for the survival or growth of a host cell transformed with the chromosomal transfer DNA or plasmid. Typical selectable markers (a) confer resistance to antibiotics or other toxic substances, e.g. ampicillin, neomycin, methotrexate, etc.; (b) complement auxotrophic deficiencies; or (c) supply critical nutrients not available from complex media, e.g. the gene encoding D-alanine racemase for Bacilli. The choice of the proper selectable marker will depend on the host cell.

The chromosomal transfer DNAs of the present invention contain a site-specific recombination site, such as the phage lambda att P site. When transformed into a bacterial host strain (such as *E. coli* B1384) which makes the enzyme integrase, integrase recognizes the att P site on the chromosomal transfer DNA and catalyses its recombination with an att site on the chromosome of the bacterial host, leading to the site-specific integration of the chromosomal transfer vector into the bacterial chromosome at the att site (integrase can catalyze a recombination between two att P and att B or two att P sites). Bacterial host cells bearing the integrated DNA are selected for on the basis of the expression of a selectable marker carried on the integrated DNA.

Thus, the integration event generally involves expression of an enzyme such as integrase which can catalyze site-specific recombination and the presence of a site recognized by the enzyme on both the chromosomal transfer DNA and the bacterial chromosome. Other site-specific recombination systems characterized by an "integrase" or similar enzyme and sites specifically recognized by the "integrase" could be used as well.

High level expression of a foreign gene integrated into the chromosome of the host cell in multiple copies is also possible, e.g., by incorporating multiple att sites in the host cell chromosome and introducing multiple chromosomal transfer DNAs into the host cell. Alternatively, a foreign gene could be amplified to produce multiple copies, e.g., by multiple rounds of selection for duplication of a marker gene carried on the integrated DNA along with the foreign gene.

An important feature of the chromosomal transfer system of the present invention is that the foreign gene is not expressed before integration; it is not operably linked to a promoter until the chromosomal transfer DNA is constructed in vitro. The chromosomal transfer DNA is constructed from two or more DNA sources. One DNA source contains the foreign gene, which is not expressed since it lacks a promoter. A second DNA source contains the promoter to which it will be operably linked on the chromosomal transfer DNA. This approach allows one to employ high copy number plasmids as DNA sources in constructing the chromosomal transfer DNA. Low copy number plasmids are more difficult to work with in the laboratory. For example, DNA minipreps may produce inadequate DNA for in vitro manipulations.

Introducing DNA into Host Cells

A variety of methods for introducing nucleic acids into host cells are known in the art, including, but not limited to, electroporation; transfection employing calcium chloride, rubidium chloride calcium phosphate, DEAE-dextran, or other substances; microprojectile bombardment; lipofection; and infection (where the vector is an infectious agent, such as a retroviral genome). See generally, Sambrook et al. (1989) and Ausubel et al. (1987).

Host Cells

The methods of the present invention are preferably used with prokaryotic host cells, although they would be applicable to eukaryotic host cells as well. Among prokaryotic hosts, *Escherichia coli* is preferred, although other prokaryotes, such as *Bacillus subtilis* or Pseudomonas may also be used.

Mammalian or other eukaryotic host cells, such as yeast, filamentous fungi, plant, insect, amphibian or avian species, may also be used. See, *Tissue Culture*, Kruse and Patterson, ed., Academic Press (1973). Useful mammalian host cell lines include, but are not limited to, VERO and HeLa cells, Chinese hamster ovary (CHO) cells, and WI38, BHK, and COS cell lines.

The invention will be better understood by reference to the following example, which is intended to merely illustrate the best mode now known for practicing the invention. The scope of the invention is not to be considered limited thereto, however.

EXAMPLE

Integration of a Chromosomal Transfer DNA Comprising a Foreign Gene into the Chromosome of *E. coli* Strain B1384

Figure 2:
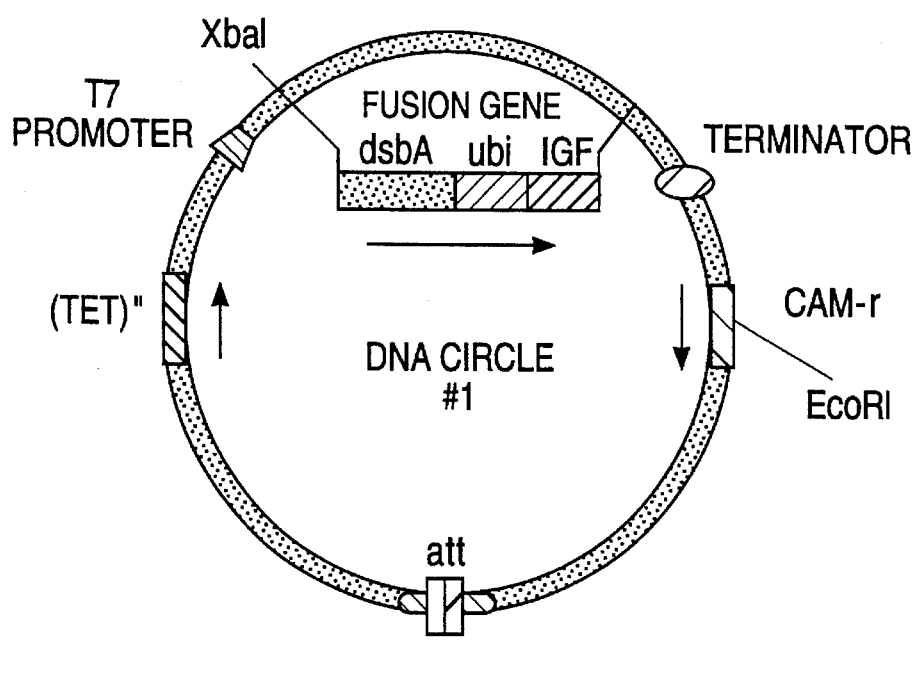
FIG. 2 shows a chromosomal transfer DNA formed from the ligation of two DNA fragments. One of the fragments contains an fusion gene comprising sequences encoding E. coli DsbA, yeast ubiquitin (beginning with a Met), and human insulin-like growth factor I ("dsbA-ubi-IGF") (not beginning with a Met), as discussed in copending U.S. patent application Ser. No. 08/100,744, filed Aug. 2, 1993. The other DNA fragment contains a T7 promoter. Both the chromosomal transfer DNA and the bacterial chromosome contain a recombination site from phage lambda, att P. The chromosomal transfer DNA is transformed into E. coli strain B1384, which makes integrase (INT) under the control of the trp promoter (P-trp). Integrase catalyses site-specific integration of the chromosomal transfer DNA into the bacterial chromosome at the att site. The trp promoter can be induced during transformation by adding 1 mM indole acrylic acid (IAA) to the medium. Cells with integrated chromosomal transfer DNA sequences are resistant to chloramphenicol (CAM-r, 10 μg/ml).

The general strategy for integrating a chromosomal transfer DNA comprising a foreign gene into the chromosome of *E. coli* is depicted schematically in FIG. 1. Two plasmids were constructed: pDM25432 contained a foreign gene of interest (in this example, an IGF-I fusion gene) lacking an operably linked bacterial promoter; pDM25423 contained a T7 promoter. By ligating restriction fragments purified from each of these vectors, a DNA circle lacking an origin of replication—a chromosomal transfer DNA—was generated. This chromosomal transfer DNA contained an antibiotic resistance gene which affords resistance to chloramphenicol (CAM-r) and a site-specific recombination site from phage lambda, att P. This chromosomal transfer DNA is transformed into a bacterial strain such as *E. coli* B1384 (Mascarenhas et al. (1983) *Virology* 124:100–108) (FIG. 2), which makes the enzyme integrase (INT) under the control of the trp promoter, which can be induced during transformation by adding 1 mM indole acrylic acid (IAA) to the medium. B1384 also contains an att P in its chromosome. Integrase recognizes the att P sites on the chromosomal transfer DNA and in the chromosome of B1384 and catalyses their recombination, leading to the site-specific integration of the chromosomal transfer DNA into the bacterial chromosome at the att P site (Weisberg et al. (1977) in *Comprehensive Virology*, vol. 8, Fraenckel-Conrat and Wagner, eds., Plenum: New York, pp. 197–258. Bacterial host cells bearing the integrated DNA are selected for on the basis of their resistance to chloramphenicol.

Figure 3:
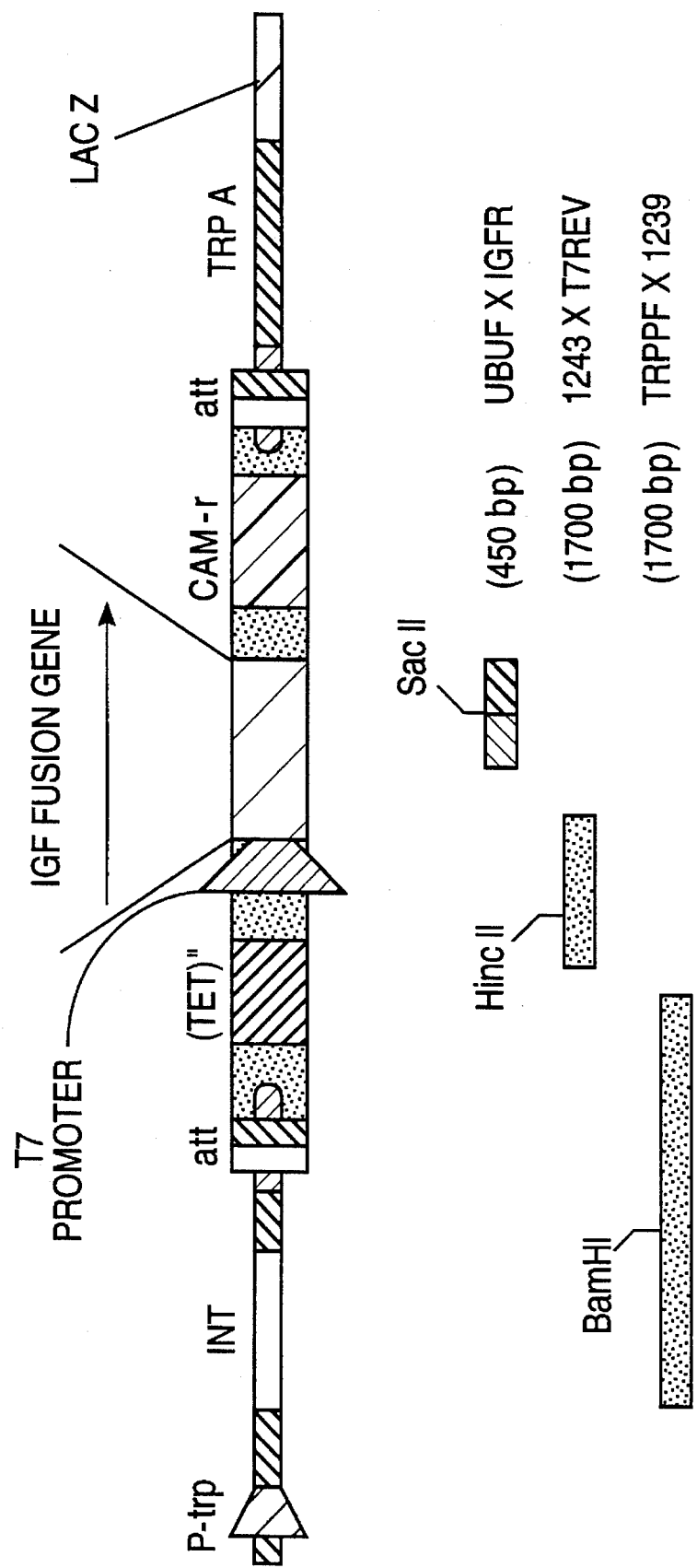
FIG. 3 shows a B1384 chromosomal integrant resulting from the process described in FIG. 2. The integration can be confirmed by amplifying host chromosomal DNA by PCR with various primer sets (e.g., UBUFxIGFR, 1243xT7REV, or TRPPFx1239), digesting the amplified fragments with the appropriate restriction enzyme (Sac II, Hinc II, or Bam HI, respectively), and sizing the products by gel electrophoresis).

Chloramphenicol-resistant chromosomal integrants were tested as summarized in FIG. 3. The presence of the integrated chromosomal transfer DNA was confirmed by amplifying host chromosomal DNA by PCR with the following primer sets (e.g., UBUF×IGFR, 1243× T7REV, or TRPPF× 1239)

| | |
|---|---|
| IGFR: | 5'... CCC ATC GAT GCA TTA AGC GGA TTT AGC CGG TTT-CAG ... 3' (SEQ ID NO:1) |
| #1239: | 5'... GCC TGA CTG CGT TAG CAA TTT AAC TGT GAT ... 3' (SEQ ID NO:2) |
| #1243: | 5'... CTG GGC TGC TTC CTA ATG CAG GAG TCG CAT ... 3' (SEQ ID NO:3) |
| #1227: | 5'... TAA TAC GAC TCA CTA TAG GGA GA ... 3' (SEQ ID NO:4) |
| TRPPF: | 5'... GAT CTG TTG ACA ATT AAT CAT CGA ACT AGT TAA CTA GTA CGC AAG TT ... 3' (SEQ ID NO:5) |
| T7REV: | 5'... TGC TAG TTA TTG CTC AGC GG ... 3' (SEQ ID NO:6) |
| CYCF1: | 5'... CAG GAT CCG ATC GTG GAG GAT GAT TAA ATG GCG AAA GGG GAC CCG CAC ... 3' (SEQ ID NO:7) |
| CYCR1: | 5'... CAG GAA GCT TAC GGC AGG ACT TTA GCG GAA AG ... 3' (SEQ ID NO:8) |
| UBUF: | 5'... GGG GCC GCG GTG GCA TGC AGA TTT TCG TCA AGA CTT TGA ... 3' (SEQ ID NO:9) |

The amplified fragments were digested with the appropriate restriction enzyme (Sac II, Hinc II, or Bam HI, respectively). The products were sized by agarose gel electrophoresis. Presence of the integrated sequences was demonstrated by amplification of:

chromosomal ubiquitin and IGF sequences, demonstrating the presence of the relevant foreign gene;

chromosomal tet and T7 sequences, demonstrating the juxtaposition of the T7 promoter and the fusion gene; and adjacent chromosomal trp and tet sequences, demonstrating insertion of the chromosomal transfer DNA at the expected location.

The chromosomal integration of the chromosomal transfer

DNA was also confirmed by the following evidence:

resistance of the bacterial host to chloramphenicol;

no plasmid DNA in DNA minipreps;

lack of beta-lactamase enzymatic activity, confirming the absence of the parental plasmids (beta-lactamase was assayed using a chromogenic substrate, 7-thienyl-2-acetamido- 3-2-4 n,n-dimethylaminophenylazopyridiniummethyl- 3-cephem-4 carboxylic acid (PADAC), as described in Schindler and Huber (1980) in *Enzyme Inhibitors*, Brodbeck, V., ed., Verlag Chemie, pp. 169–176; and segregation analysis: Isolates were grown in L broth with or without 1 mM IAA at 37° C. overnight and plated on LB agar plates. Single colonies from each culture were tested for retention of chloramphenicol resistance. 100% retention was observed from cultures without IAA; 11% retention was observed in cultures with IAA.

Six of seven isolates tested showed the expected phenotypes.

B1384 does not contain the gene for T7 RNA polymerase. In order to test the expression of the chromosomal constructs, P1 lysates were prepared on each of the six strains carrying the integrated DNA and used to transduce strain W3110DE3 to chloramphenicol resistance. Strain W3110DE3 carries the T7 RNA polymerase gene under the control of the lac promoter. It is also Gal$^+$, unlike B1384. Transductants were therefore selected on galactose minimal plates containing 20 µg/ml chloramphenicol. Single colonies from each transduction experiment (independent donors) were purified and tested further.

The results obtained were identical in all six independent cases: the chromosomal transfer DNA was transferred with high frequency to a new location on the bacterial chromosome, the att sites flanking the prophage in W3110DE3. This was confirmed by chloramphenicol resistance;

no plasmid DNA in DNA minipreps;

i21 immunity (DE3 lysogen; phage lysates were plated on bacterial lawns by standard techniques);

Gal$^+$ (i.e., growth on galactose minimal plates);

expression of IGF protein under lac control (expression and analysis carried out as described in Example 1 of copending U.S. patent application Ser. No. 08/101,506, filed Aug. 2, 1993).

Chromosomal DNA from the six strains ("integrants") was digested to completion with Bgl II and Nco I and a Southern blot of the digested DNA was probed with a labelled 0.6 kb dsbA DNA probe which covers the entire gene sequence coding for mature DsbA (Bardwell et al. (1991) *Cell* 67:581–589; see also Kamitani et al. (1992) *EBMO J.* 11:57–62). Each of the six integrants contained insertions; the blots demonstrated the existence of several double insertions, one single insertion, and one (isolate WB3-6) apparently duplicated double (i.e. triple) insertion.

Figure 4:
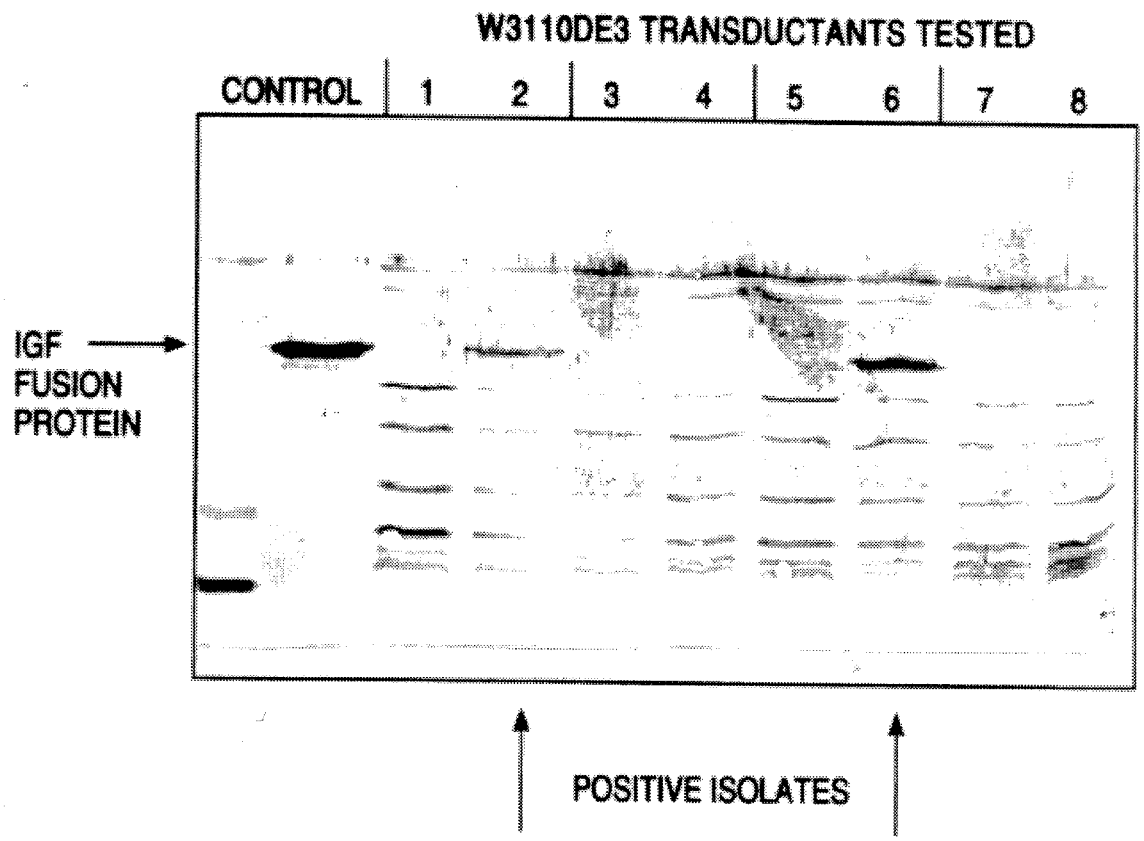
FIG. 4 shows a Western blot of whole cell lysates of chloramphenicol resistant W3110DE3 transductants. Also included are protein size markers (far left lane) and IGF fusion protein (control).

The six integrants were tested for expression of the IGF fusion protein after induction with isopropyl-β-thiogalactopyranoside (IPTG). Cells were induced with IPTG for two hours and whole cell extracts for the induced integrants, as well as size markers and an IGF fusion protein control, were separated by 12% SDS-PAGE, Western blotted, and reacted with polyclonal anti-IGF sera (see Example 1 of copending U.S. patent application Ser. No. 08/101,506, filed Aug. 2, 1993) (FIG. 4). Isolate WB3-6 (FIG. 4, lane 6) showed the highest levels of expression of the IGF fusion protein. An induced band of the same size was also seen on Coomassie blue-stained gels.

Figure 5:
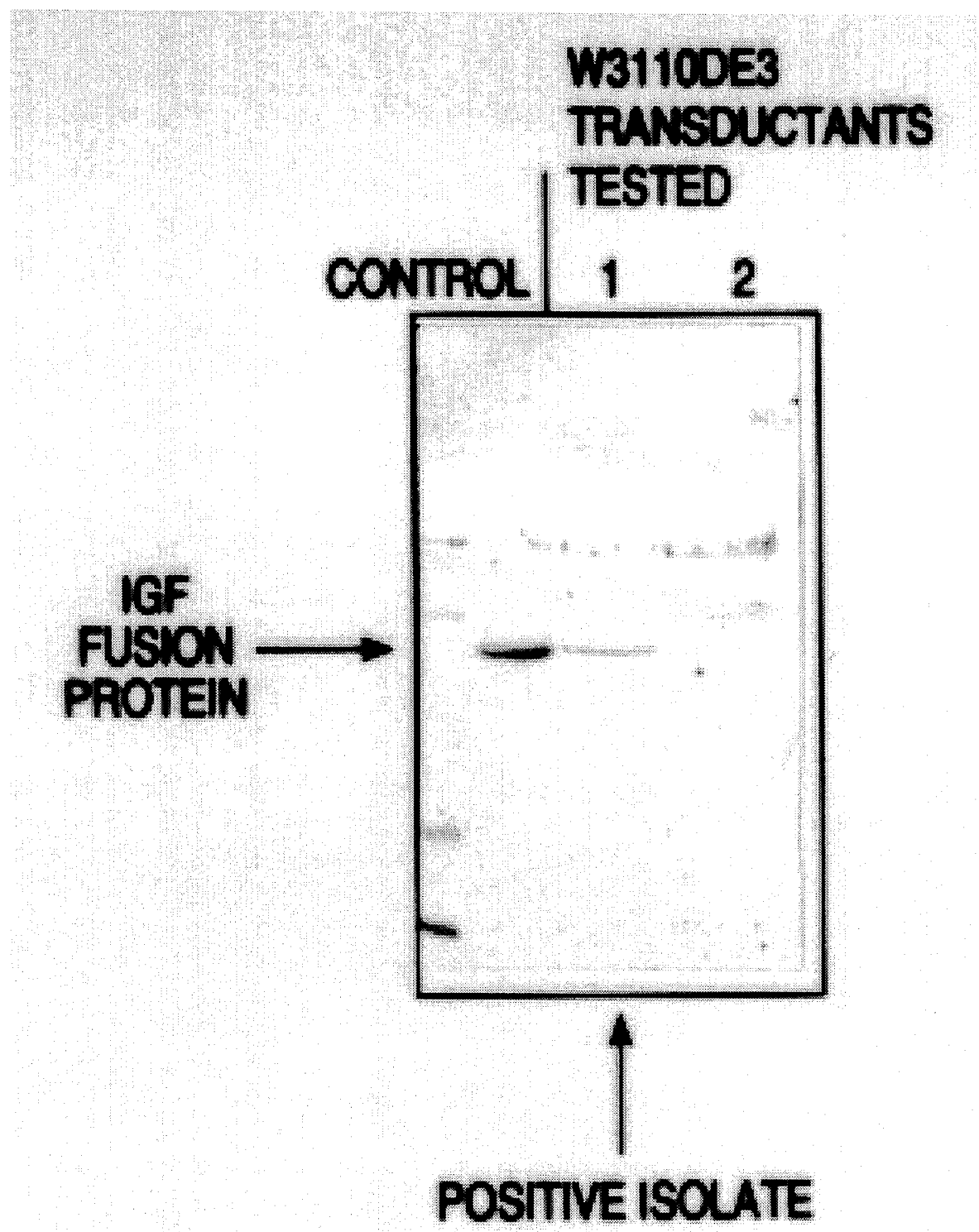
FIG. 5 shows a Western blot of whole cell lysates of kanamycin resistant transductants.
Figure 6:
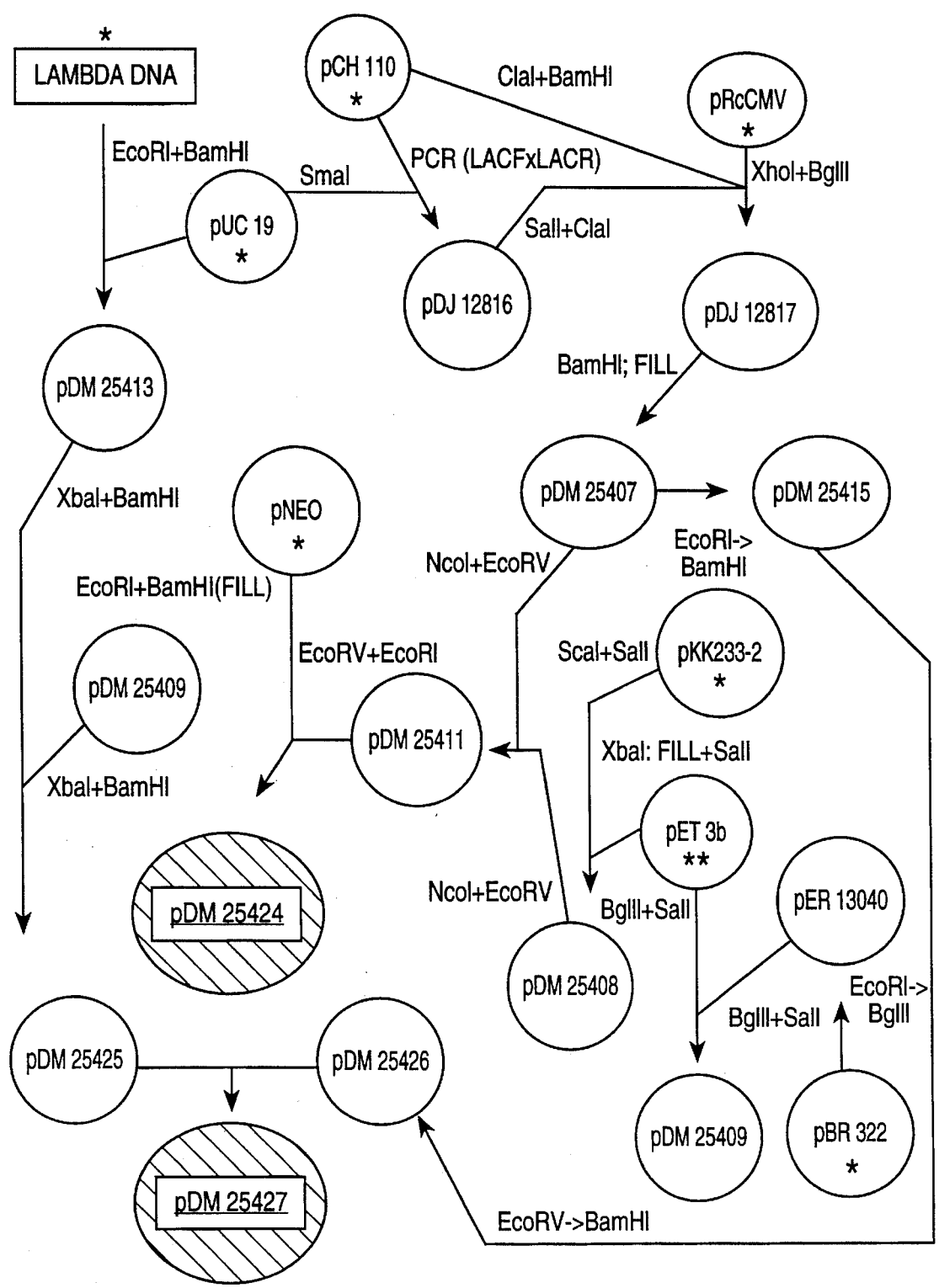
FIGS. 6–9 show the plasmid genealogy of chromosomal transfer DNA.
Figure 7:
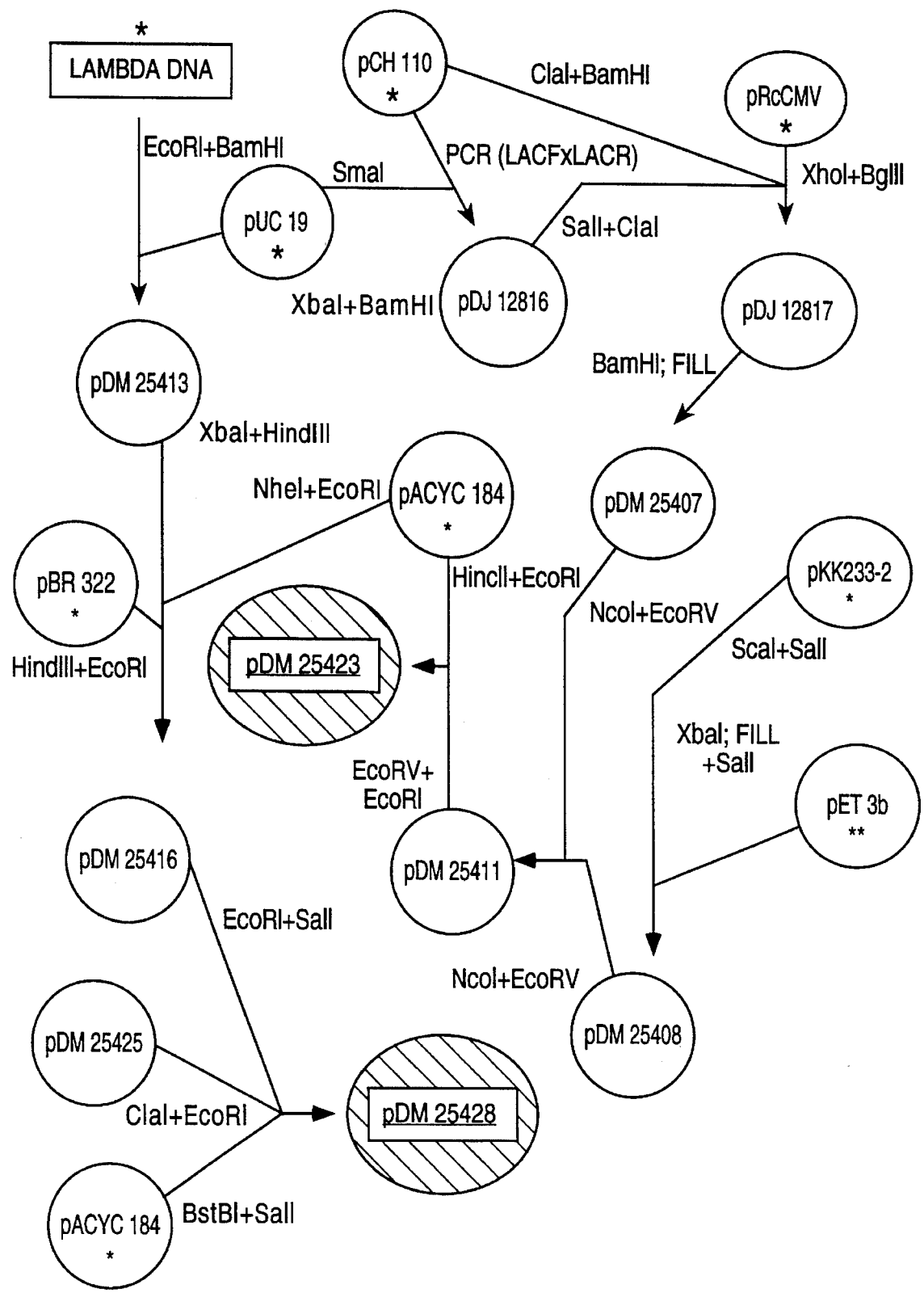
Figure 8:
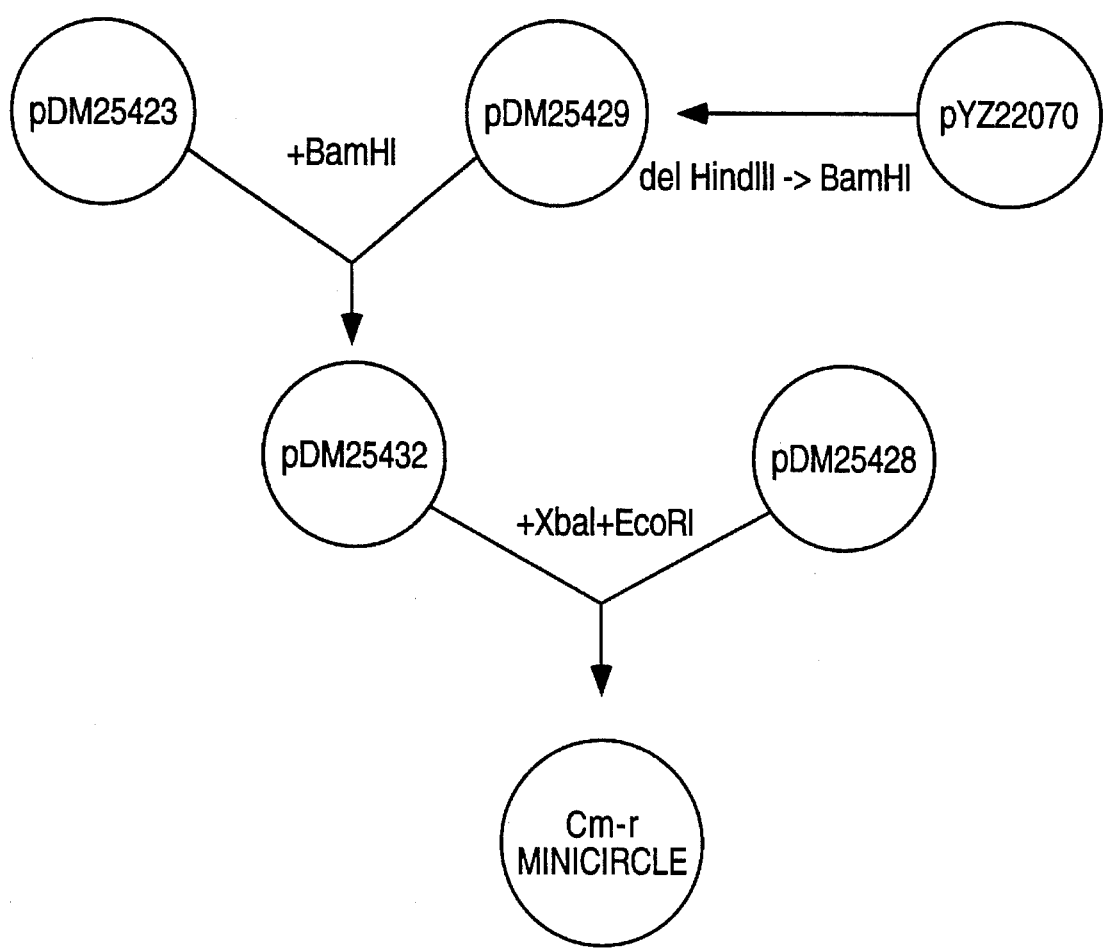
Figure 9:
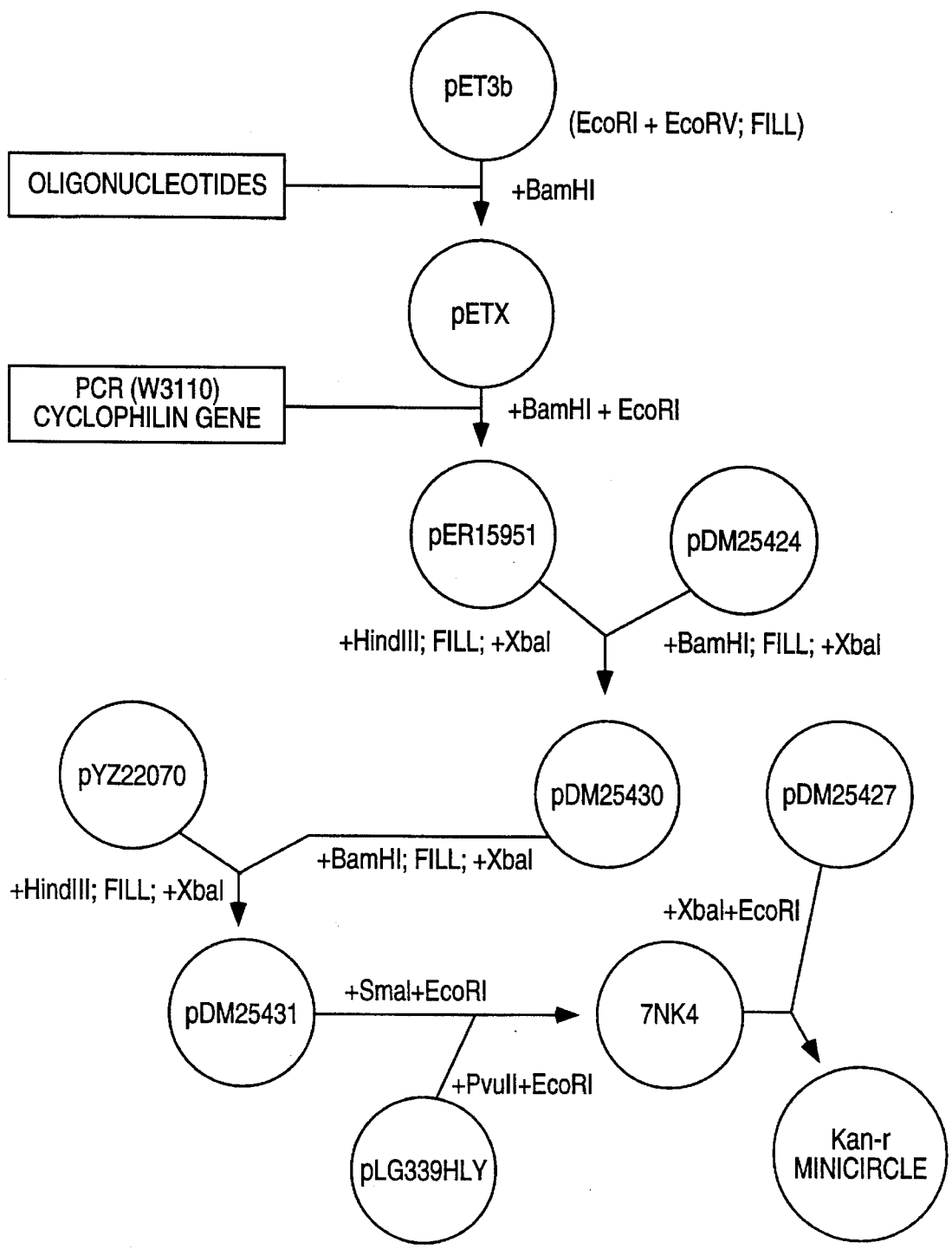

A different binary system was used to generate a chromosomal transfer DNA carrying a kanamycin resistance marker. The plasmids used, pDM25424 and pDM25427, are described in the figures. The configuration and location of the insert were confirmed by PCR, giving results which were virtually identical to those described above. After transduction into the W3110DE3 background, several individual isolates were obtained which expressed the IGF fusion protein at levels that could easily be detected by Western blotting (FIG. 5). Procedures used were identical to the ones described above for the chloramphenicol-resistant isolates, except that the antibiotic and resistance gene employed were kanamycin instead of chloramphenicol. Purified fusion protein was the control. Lanes 1 and 2 contain whole cell lysates from two transducted isolates.

The construction of the vectors employed in the two binary systems is summarized in FIGS. 6–9. The sources for the plasmids employed were: pBR322, pUC18, pUC19, pKK233-2, ptRC99A, pCH110, and pNEO (Pharmacia, Piscataway, N.J.); pLG339HLY (Dr. Barry Holland, Institute de Génétiques et Microbiologie, Université Paris-Sud); pRc-CMV (Invitrogen, San Diego, Calif.); pACYC177 and pACYC184 (New England Biolabs, Beverly, Mass.); pET3b (Studier and Moffat (1986) *J. Mol. Biol.* 189:113–130); pYZ22070 (described in Example 1 of co-pending U.S. patent application Ser. No. 08/100,744, filed Aug. 2, 1993).

*E. coli* K-12 strain W3110 was obtained from B. Bachmann, ECGSC, Yale University. It was lysogenized with the DE3 defective phage as described by Studier and Moffat (1986) *J. Mol. Biol.* 198:113–130. W3110DE3 was one such lysogen. The cyclophilin gene was amplified by the polymerase chain reaction (PCR) from w3110 using the primers CYCF1 and CYCR1 (see above).

All patents and patent applications cited in this specification are incorporated herein by reference to the same extent as if each individual patent or patent application was specifically and individually indicated to be incorporated by reference.

It should be apparent that one having ordinary skill in the art would be able to surmise equivalents to the claimed invention which would be within the spirit of the description above. Those equivalents are to be included within the scope of the present invention.

What is claimed is:

1. A method for introducing a non-bacterial gene of interest into a chromosome of a host cell comprising the steps of:

ligating a restriction fragment from a first plasmid vector with a restriction fragment from a second plasmid vector, wherein the first plasmid vector comprises a first origin of replication and a non-bacterial gene of interest lacking an operably linked promoter, the second plasmid vector comprises a second origin of replication and a promoter, the origins of replication and the promoter are functional in the host cell, and either said first plasmid vector or said second plasmid vector comprises a site-specific recombination site, thereby producing a chromosomal transfer DNA comprising a non-bacterial gene of interest operably linked to a promoter functional in the host cell, a selectable marker, and a first site-specific recombination site, and lacking an origin of replication;

transferring the chromosomal transfer DNA into a host cell, the host cell comprising a chromosome, the chromosome comprising a second site-specific recombination site and a DNA sequence encoding an enzyme which is capable of catalyzing the site-specific recombination of the first and second recombination sites;

expressing the enzyme, thereby causing integration of the chromosomal transfer DNA into the chromosome of the host cell at the second site-specific recombination site; and selecting for host cells having an integrated chromosomal transfer DNA;

whereby the non-bacterial gene of interest is at no time operably linked to a functional promoter in a multicopy number vector.

\* \* \* \* \*